United States Patent
Carpenter

(10) Patent No.: US 9,480,548 B2
(45) Date of Patent: *Nov. 1, 2016

(54) EMBOLIC PROTECTION DEVICE AND METHOD OF USE

(75) Inventor: Judith T. Carpenter, Radnor, PA (US)

(73) Assignee: Edwards Lifesciences AG, Nyon (CH)

( * ) Notice: Subject to any disclaimer, the term of this patent is extended or adjusted under 35 U.S.C. 154(b) by 834 days.

This patent is subject to a terminal disclaimer.

(21) Appl. No.: 12/440,839

(22) Filed: Mar. 11, 2009

(65) Prior Publication Data

US 2010/0211095 A1  Aug. 19, 2010

Related U.S. Application Data

(63) Continuation-in-part of application No. PCT/US2007/078170, filed on Sep. 11, 2007, which is a continuation-in-part of application No. 11/518,865, filed on Sep. 11, 2006, now Pat. No. 8,460,335.

(51) Int. Cl.
*A61M 29/00* (2006.01)
*A61F 2/01* (2006.01)

(52) U.S. Cl.
CPC .......... *A61F 2/013* (2013.01); *A61F 2002/011* (2013.01); *A61F 2002/016* (2013.01); *A61F 2002/018* (2013.01); *A61F 2230/005* (2013.01);

(Continued)

(58) Field of Classification Search
CPC .... A61F 2/01; A61F 2/013; A61F 2002/016; A61F 2002/011; A61F 2002/015–2002/018; A61B 17/0057; A61B 17/22031; A61B 17/22034; A61B 17/22035; A61B 17/221; A61B 17/12113; A61B 17/22; A61B 17/24; A61B 17/26; A61B 2017/00358; A61B 2017/0061; A61B 2017/00615; A61B 2017/2212; A61B 2017/2217; A61B 2017/32056
USPC ................ 606/200, 194, 113–114, 127–128; 623/1.15, 2.11
See application file for complete search history.

(56) References Cited

U.S. PATENT DOCUMENTS

| 4,619,246 A | 10/1986 | Molgaard-Nielsen et al. |
| 5,634,942 A | 6/1997 | Chevillon et al. |

(Continued)

FOREIGN PATENT DOCUMENTS

WO   WO 2006/076505 A2   7/2006

OTHER PUBLICATIONS

U.S. Appl. No. 12/892,767, filed Sep. 28, 2010, Belson.

(Continued)

*Primary Examiner* — Elizabeth Houston
*Assistant Examiner* — Lindsey Bachman
(74) *Attorney, Agent, or Firm* — Guy Cumberbatch; David L. Hauser; AnneMarie Kaiser

(57) ABSTRACT

There is disclosed a porous emboli deflector for preventing cerebral emboli while maintaining cerebral blood flow during an endovascular or open surgical procedure. The device prevents the entrance of emboli of a size able to cause stroke (greater than 100 microns in the preferred embodiment) from entering either the right or left carotid arteries by deflecting emboli downstream in the blood flow. The device can be placed prior to any manipulation of the heart or aorta allowing maximal protection of the brain during the index procedure. The device has a low profile within the aorta which allows sheaths, catheters, or wires used in the index procedure to pass. Also disclosed are methods for insertion and removal of the device.

16 Claims, 28 Drawing Sheets

(52) U.S. Cl.
CPC  *A61F 2230/0006* (2013.01); *A61F 2230/0008* (2013.01); *A61F 2230/008* (2013.01); *A61F 2230/0019* (2013.01); *A61F 2230/0021* (2013.01); *A61F 2230/0093* (2013.01)

(56) References Cited

U.S. PATENT DOCUMENTS

| | | | |
|---|---|---|---|
| 5,662,671 | A | 9/1997 | Barbut et al. |
| 5,695,519 | A | 12/1997 | Summers et al. |
| 5,769,816 | A | 6/1998 | Barbut et al. |
| 5,911,734 | A | 6/1999 | Tsugita et al. |
| 5,989,281 | A | 11/1999 | Barbut et al. |
| 5,993,469 | A | 11/1999 | McKenzie et al. |
| 6,027,520 | A | 2/2000 | Tsugita et al. |
| 6,042,598 | A | 3/2000 | Tsugita et al. |
| 6,117,154 | A | 9/2000 | Barbut et al. |
| 6,152,946 | A | 11/2000 | Broome et al. |
| 6,235,045 | B1 | 5/2001 | Barbut et al. |
| 6,245,088 | B1* | 6/2001 | Lowery ............... 606/200 |
| 6,251,122 | B1 | 6/2001 | Tsukernik |
| 6,254,563 | B1 | 7/2001 | Mackoviak et al. |
| 6,258,120 | B1 | 7/2001 | McKenzie et al. |
| 6,270,513 | B1 | 8/2001 | Tsugita et al. |
| 6,336,934 | B1 | 1/2002 | Gilson et al. |
| 6,346,116 | B1 | 2/2002 | Brooks et al. |
| 6,348,063 | B1 | 2/2002 | Yassour et al. |
| 6,361,545 | B1 | 3/2002 | Macoviak et al. |
| 6,371,935 | B1 | 4/2002 | Macoviak et al. |
| 6,371,969 | B1 | 4/2002 | Tsugita et al. |
| 6,375,670 | B1 | 4/2002 | Greenhalgh |
| 6,391,044 | B1 | 5/2002 | Yadav et al. |
| 6,395,014 | B1 | 5/2002 | Macoviak et al. |
| 6,423,086 | B1 | 7/2002 | Barbut et al. |
| 6,447,530 | B1 | 9/2002 | Ostrovsky et al. |
| 6,499,487 | B1 | 12/2002 | McKenzie et al. |
| 6,511,497 | B1 | 1/2003 | Braun et al. |
| 6,537,297 | B2 | 3/2003 | Tsugita et al. |
| 6,547,760 | B1 | 4/2003 | Samson et al. |
| 6,626,937 | B1 | 9/2003 | Cox |
| 6,645,221 | B1 | 11/2003 | Richter |
| 6,673,089 | B1 | 1/2004 | Yassour et al. |
| 6,695,811 | B2 | 2/2004 | Samson et al. |
| 6,695,864 | B2 | 2/2004 | Macoviak et al. |
| 6,706,053 | B1 | 3/2004 | Boylan et al. |
| 6,726,702 | B2 | 4/2004 | Khosravi |
| 6,740,112 | B2 | 5/2004 | Yodfat et al. |
| 6,866,680 | B2 | 3/2005 | Yassour et al. |
| 6,962,598 | B2 | 11/2005 | Linder et al. |
| 6,989,019 | B2 | 1/2006 | Mazzocchi et al. |
| 6,994,092 | B2 | 2/2006 | Van der Berg et al. |
| 7,083,633 | B2 | 8/2006 | Morrill et al. |
| 7,112,213 | B2 | 9/2006 | Maahs |
| 7,144,408 | B2 | 12/2006 | Keegan et al. |
| 7,169,154 | B1* | 1/2007 | Que et al. ............... 606/127 |
| 7,172,614 | B2 | 2/2007 | Boyle |
| 7,174,636 | B2 | 2/2007 | Lowe |
| 7,217,255 | B2 | 5/2007 | Boyle et al. |
| 7,229,463 | B2 | 6/2007 | Sutton et al. |
| 7,229,464 | B2 | 6/2007 | Hanson et al. |
| 7,232,453 | B2 | 6/2007 | Shimon |
| 7,235,061 | B2 | 6/2007 | Tsugita |
| 7,241,304 | B2 | 7/2007 | Boyle et al. |
| 7,241,305 | B2 | 7/2007 | Ladd |
| 7,244,267 | B2 | 7/2007 | Huter et al. |
| 7,252,675 | B2 | 8/2007 | Denison et al. |
| 7,261,727 | B2 | 8/2007 | Thielen et al. |
| 7,303,575 | B2 | 12/2007 | Ogle |
| 7,323,001 | B2 | 1/2008 | Clubb et al. |
| 7,367,985 | B2 | 5/2008 | Mazzocchi et al. |
| 7,604,650 | B2 | 10/2009 | Bergheim |
| 7,618,446 | B2 | 11/2009 | Andersen et al. |
| 7,670,356 | B2 | 3/2010 | Mazzocchi |
| 7,727,253 | B2* | 6/2010 | Ackerman et al. ............... 606/200 |

| | | | |
|---|---|---|---|
| 2002/0077596 | A1* | 6/2002 | McKenzie et al. ........... 604/104 |
| 2002/0128679 | A1 | 9/2002 | Turovskiy et al. |
| 2002/0128680 | A1 | 9/2002 | Pavlovic |
| 2002/0138094 | A1 | 9/2002 | Borillo et al. |
| 2002/0143362 | A1 | 10/2002 | Macoviak et al. |
| 2002/0161394 | A1 | 10/2002 | Macoviak et al. |
| 2002/0169437 | A1 | 11/2002 | Macoviak et al. |
| 2002/0169474 | A1 | 11/2002 | Kusleika et al. |
| 2003/0120304 | A1 | 6/2003 | Kaganov et al. |
| 2003/0125801 | A1 | 7/2003 | Yodfat et al. |
| 2003/0158574 | A1 | 8/2003 | Esch et al. |
| 2003/0208224 | A1 | 11/2003 | Broome |
| 2003/0220667 | A1 | 11/2003 | Van der Burg et al. |
| 2004/0010307 | A1 | 1/2004 | Grad et al. |
| 2004/0010308 | A1 | 1/2004 | Zafrir-Pachter |
| 2004/0024416 | A1 | 2/2004 | Yodfat et al. |
| 2004/0034386 | A1 | 2/2004 | Fulton et al. |
| 2004/0088002 | A1 | 5/2004 | Boyle et al. |
| 2004/0093014 | A1 | 5/2004 | Ho et al. |
| 2004/0111111 | A1 | 6/2004 | Lin |
| 2004/0158281 | A1 | 8/2004 | Boylan et al. |
| 2004/0167568 | A1 | 8/2004 | Boyle et al. |
| 2004/0167613 | A1 | 8/2004 | Yodfat et al. |
| 2004/0215167 | A1 | 10/2004 | Belson |
| 2004/0243174 | A1* | 12/2004 | Ackerman et al. ........... 606/200 |
| 2005/0085847 | A1 | 4/2005 | Galdonik et al. |
| 2005/0119688 | A1 | 6/2005 | Bergheim |
| 2005/0267516 | A1 | 12/2005 | Soleimani et al. |
| 2005/0283185 | A1 | 12/2005 | Linder et al. |
| 2006/0015138 | A1 | 1/2006 | Gertner |
| 2006/0015141 | A1 | 1/2006 | Linder et al. |
| 2006/0058833 | A1 | 3/2006 | VanCamp et al. |
| 2006/0129180 | A1 | 6/2006 | Tsugita et al. |
| 2006/0161241 | A1* | 7/2006 | Barbut et al. ............... 623/1.15 |
| 2006/0241678 | A1 | 10/2006 | Johnson et al. |
| 2006/0253148 | A1 | 11/2006 | Leone et al. |
| 2006/0287670 | A1 | 12/2006 | Pal |
| 2006/0293706 | A1 | 12/2006 | Shimon |
| 2007/0043435 | A1 | 2/2007 | Seguin et al. |
| 2007/0123931 | A1 | 5/2007 | Gilson et al. |
| 2007/0135834 | A1 | 6/2007 | Clubb et al. |
| 2007/0270901 | A1 | 11/2007 | Shimon et al. |
| 2008/0004688 | A1 | 1/2008 | Spenser et al. |
| 2008/0051807 | A1 | 2/2008 | St. Goar et al. |
| 2008/0065145 | A1 | 3/2008 | Carpenter |
| 2008/0065146 | A1 | 3/2008 | Mazzocchi et al. |
| 2008/0065147 | A1 | 3/2008 | Mazzocchi et al. |
| 2008/0086149 | A1* | 4/2008 | Diamant et al. ............... 606/113 |
| 2008/0109055 | A1 | 5/2008 | Hlavka et al. |
| 2008/0114440 | A1 | 5/2008 | Hlavka et al. |
| 2008/0140110 | A1 | 6/2008 | Spence |
| 2008/0140189 | A1 | 6/2008 | Nguyen et al. |
| 2008/0255603 | A1 | 10/2008 | Naor et al. |
| 2008/0275489 | A1 | 11/2008 | Kinst et al. |
| 2009/0062908 | A1 | 3/2009 | Bonhoeffer et al. |
| 2009/0326575 | A1* | 12/2009 | Galdonik et al. ............... 606/200 |
| 2010/0179583 | A1 | 7/2010 | Carpenter et al. |
| 2010/0179584 | A1 | 7/2010 | Carpenter et al. |
| 2010/0179585 | A1 | 7/2010 | Carpenter et al. |
| 2010/0179647 | A1 | 7/2010 | Carpenter et al. |
| 2010/0312268 | A1 | 12/2010 | Belson |
| 2011/0295304 | A1* | 12/2011 | Jonsson ............... 606/200 |

OTHER PUBLICATIONS

U.S. Appl. No. 12/836,508, filed Jul. 14, 2010, Carpenter.
International Preliminary Report on Patentability, PCT/US07/78170 mailed Mar. 17, 2009 in 5 pages.
International Search Report dated Mar. 2, 2010 PCT/US2010/020530 in 11 pages.
Office Action dated Mar. 5, 2010, U.S. Appl. No. 11/518,865 in 7 pages.
Office Action dated Aug. 3, 2010, U.S. Appl. No. 11/518,865 in 9 pages.

* cited by examiner

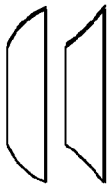
FIG.5AA
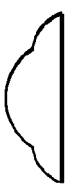
FIG.5BB
FIG.5CC
FIG.5DD
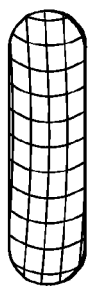
FIG.5EE
FIG.5FF
FIG.5GG
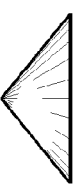
FIG.5HH
FIG.5II
FIG.5JJ
FIG.5KK

EMBOLIC PROTECTION DEVICE AND METHOD OF USE

CROSS REFERENCE TO RELATED APPLICATIONS

This application is a continuation-in-part of International Application No. PCT/US2007/078170, filed on Sep. 11, 2007, which published in English as International Publication No. WO 2008/033845 A2 on Mar. 20, 2008, which is a continuation-in-part of U.S. patent application Ser. No. 11/518,865, filed on Sep. 11, 2006, now U.S. Pat. No. 8,460,335.

RELATED APPLICATIONS

The entirety of US Published Application US2008/0065145 A1 is incorporated by reference herein, as if set forth fully herein.

The entirety of International Application WO2008/033845 A2 is incorporated by reference herein, as if set forth fully herein. In the event that this application is deemed not to be a US Published Application, the full text is set forth in the Appendix hereto, which is a part of this application.

FIELD OF THE INVENTION

Disclosed are porous emboli deflectors for blocking cerebral emboli while maintaining cerebral blood flow during an endovascular or open surgical procedure.

BACKGROUND OF THE INVENTION

Endovascular procedures are being used more and more frequently to treat various cardiac and vascular surgical problems. Blocked arteries can be treated with angioplasty, endarterectomy, and/or stenting, using minimally invasive endovascular approaches. Aneurysms can be repaired by endovascular techniques. Another use for endovascular surgery is the treatment of cardiac valvular disease. Valvuloplasties are already being done endovascularly and percutaneous valve replacement is being tested in the United States and two devices are already approved for use in Europe. A major problem which is common to all these endovascular manipulations is that plaque found in the diseased vessels and valves can be dislodged and result in embolization. A major drawback to endovascular treatment of cardiac valves or the thoracic aorta is that the dislodged debris can embolize into the carotid vessels resulting in catastrophic consequences such as stroke or even death. Any procedure involving the passage of catheters across the aortic arch carries this risk of causing carotid emboli. Attempts have been made to protect the cerebral vasculature with filters and other devices. The majority of devices described are filters. The problems with filters include difficulty in placement and retrieval as well as the possibility that a filter will fill abruptly causing blockage of the artery prior to removal of the filter. Cerebral protection requires placement of filters in the carotid arteries, which has the additional drawback of manipulation of the carotid vessels during filter placement while the cerebral vasculature is still unprotected. The risk of stroke for a carotid arteriogram done by cannulation of the carotid artery is 1% compared to an arteriogram done from injection into the aorta without selective cannulation which carries minimal risk. The risk of cannulating a carotid artery, navigating a catheter containing a filter into position, and deploying the filter would likely carry an even higher stroke risk. Patients requiring cardiac or aortic arch procedures are high risk candidates for having carotid disease. These procedures simultaneously place both carotid arteries at risk for emboli. The chance of causing a stroke by the placement of a protective device into both carotid arteries makes the risk of using these devices prohibitive. The time and skill necessary to selectively cannulate both carotid arteries for filter placement has also contributed to the decision not to use them despite the stroke risk of unprotected cardiac and aortic arch procedures.

Only a small number of devices have recently been developed which are designed to protect both carotid arteries at the same time. One device to date has come to market which protects both carotid arteries from emboli. The Edwards Lifesciences' EMBOL-X is a device designed for use in open heart surgery during cardiopulmonary bypass. The device is a filtering screen inserted directly into the ascending aorta immediately beyond the heart, similar to a dryer vent screen. This screen filters all blood exiting the heart and bypass machine prior to allowing it to pass to the downstream circulation. Limitations of this device include its applicability only to open heart surgery, excluding its use in the vast array of endovascular procedures requiring protection. Adoption of the device has been hampered by ease of use, as operators often find it cumbersome. The device could not be adapted to endovascular procedures as the EMBOL-X completely spans the aorta. Thus wires or catheters could not pass by it without breaking its protective seal. It has found limited adoption, and is chiefly employed for high risk patients undergoing open heart surgery. NeuroSonix Ltd. has developed the EmBlocker™, an ultrasound based scheme to deflect emboli away from the cerebral circulation during open cardiac procedures. An ultrasound probe is placed through the sternal wound and ultrasonic energy is directed at the blood flow in the aortic arch with the intent of deflecting emboli away from the cerebral circulation. Another proposed version for use in endovascular procedures is in the form of an externally applied "collar" around the neck of the patient, which would apply ultrasound through the neck with the hope of deflecting embolic particles away from the carotid circulation. It is known that the ultrasound beam can be tolerated only for brief periods of time and that it is turned off and on at different points during procedures. Thus there would be a lack of complete protection from beginning to end of an open heart procedure or endovascular procedure.

One additional device being developed for aortic embolic protection is the SagaX AEPD which is placed in the aorta through a femoral artery and secured in position with wire bows pressing against the wall of the aorta and another vessel wall. A key difference and disadvantage of this device is that, when it is positioned to cover the vessels of the aortic arch, one of its bows spans the aorta. Although a catheter from the index procedure might be able to pass through the open loop of the bow there is the possibility for entanglement, of dislodging the device, or of pressing against the bow causing damage to the aortic wall. Another difference and disadvantage of this device includes its delivery through the as yet unprotected aorta. The device is delivered across the aortic arch, which could cause emboli, and is manipulated into position in the arch with deployment of its bows against vessel walls while the aorta is unprotected. Other differences and disadvantages include possible difficulty in positioning, difficulty in sealing it in position, and possible trauma to the vessel walls from the pressure of the bows.

The Embrella Device described in this patent is an embolic protection system intended to reduce the amount of embolic material that may enter the carotid arteries during endovascular procedures involving the passage of catheters across the aortic arch. It may also be used for other endovascular procedures and open surgical procedures. It has many advantages for use with endovascular cardiac and aortic procedures. It is placed through an artery of the arm separate from the femoral insertion site of index procedure catheters and devices. It uses a 6 French sheath. It is easy to place using standard Seldinger technique. It is easy to deploy in the aorta where it self-aligns and can be secured in position covering the ostia of both the brachiocephalic and left common carotid arteries. It is able to be placed before the index procedure is begun and can remain in place, providing embolic protection, until the procedure is completed. It has a very low profile in the aorta so that wires, catheters, and sheaths can pass by it without interaction. It is able to deflect emboli greater than 100 microns in diameter away from the carotid arteries thus protecting the patient from potentially devastating neurological consequences of these emboli. Because it is designed so that one size fits all, it can be kept available in stock.

SUMMARY OF THE INVENTION

The Embrella shield deploys via a brachial or radial approach into the aorta to cover the ostia of the brachiocephalic and left common carotid arteries. The purpose of the device is to shield the carotid arteries from embolic debris that is knocked loose during procedures carried out in the aorta and/or heart while allowing blood flow to the brain through these arteries. The device is intended to be collapsed into a loader, backloaded past the hemostasis valve of a 6F sheath, and then advanced through the sheath until it deploys in the aorta and is positioned for deflection. The device has an oval shape which self-aligns in the aorta and allows for coverage of the ostia of both the brachiocephalic and left common carotid arteries.

BRIEF DESCRIPTION OF THE DRAWINGS

The invention will now be explained and other advantages and features will appear with reference to the accompanying schematic drawings wherein.

DETAILED DESCRIPTION OF THE PREFERRED EMBODIMENTS

Nitinol Frame

Figure 1:
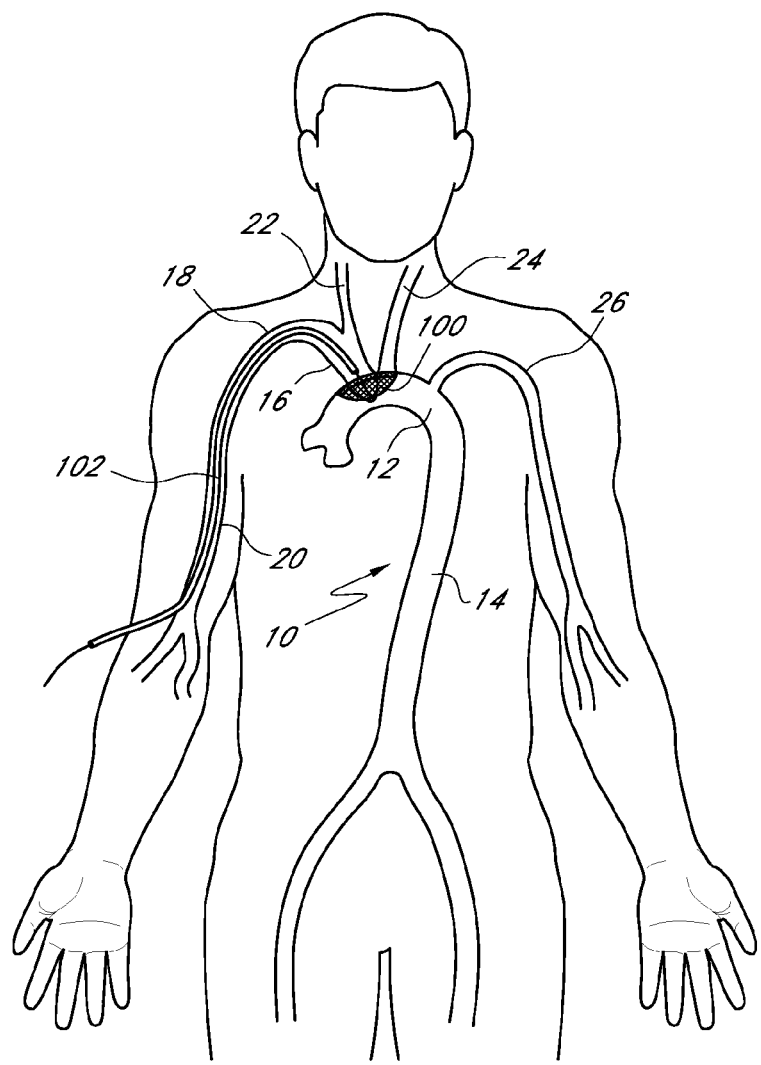
FIG. 1 depicts brachial artery insertion of the deflector of the present invention.

A preferred embodiment of the nitinol frame is built from a single laser-cut piece of material. The frame can also be built from separate wires that are formed and welded together. The frame is formed so that it is intentionally bent back into a boat-like shape to press against the aortic wall when it is deployed. When laid flat, the frame measures 60 mm along its long axis to ensure coverage of both the brachiocephalic and left common carotid artery over a wide range of anatomies. It could also be made a different size. There are three thicknesses along the perimeter of the frame to provide varying stiffness as needed. The thinnest sections at each end are critical to function—the way the device collapses would cause the nitinol to permanently deform if they were thicker, which is a gating issue for working in the 6F profile. The deploy/collapse sequence emanates from the central struts and continues to the tips of the device. One benefit of this design is that the physician can visualize the tips as they deploy, somewhat like a blooming flower.

Another benefit is that the device does not reach straight across the aorta or touch the wall of the lesser curvature of the aorta while deploying. There are holes in the frame for radiopaque markers to be loaded—one at each petal tip and one on the shaft for alignment with the sheath marker. The radiopaque markers on the frame tips and on the shaft as well as the visibility of the nitinol frame itself aid in placement guidance. The frame is attached to the shaft via an interlocking feature cut into each of the central struts near the proximal end. Acting somewhat like a puzzle piece, this mechanical engagement ensures sufficient strength for deployment, manipulation and retrieval of the device. A segment of hypodermic tubing is crimped and bonded in place over the connection for added stability. This also houses the shaft RO marker and proximal end of the sutures that aid in retrieval.

The frame of the device of the present invention may alternatively be formed by injection molding, cold forming, casting, or any other suitable method, or combination of methods, or the frame may be formed to assume the desired conformation upon inflation, heating, cooling, or exposure to body fluids.

The radiopaque markers disposed on the frame may be plated to the frame surface, may be painted thereon, dyed, applied as a wire wrap or coil, or any other suitable radiopaque technique. The position of the markers may be offset from the major axis of the frame to permit proper folding of the frame.

Membrane:

The membrane is a laser drilled polyurethane (100.mu. pore size) film that allows for blood flow, but deflects emboli of critical size. The membrane is heparin coated. It may also be uncoated or coated with another substance. The attachment of the membrane to the nitinol frame in the preferred embodiment of the device is accomplished by wrapping the polyurethane around the wire and heat bonding it to itself. Other options for attachment include using a polyurethane dispersion to coat the nitinol frame then heat bonding the film to it, adhesive bonding, suturing, and/or ultrasonic welding.

The membrane of the device may be formed from materials including, but not limited to PET, PETE, PETN, PTFE, EPTFE with a high internodal distance, and the membrane may be optionally filled or coated with a radiopaque material, and may be woven, airlaid, or film-formed. The membrane may be attached to the frame by any suitable means including chemical bonding, heat bonding, sutures, and interference fit such as by a double frame trapping the membrane material. The membrane may have either uniform or non-uniform pore sizes and areal distributions and patterns.

Shaft:

The shaft is constructed of a solid nitinol wire which gives it flexibility and strength. The shaft is 110 cm in length to allow for manipulation through sheaths as long as 90 cm. It could also be of different length. It has a minimally sized (0.035" diameter) so that the interventionalist can flush contrast between the shaft and the sheath to confirm position of the shield.

Alternatively, the shaft may be any other suitable material including polymer or stainless steel, and may be solid, coil, or composite. Optionally, the shaft may be provided with a handle disposed at its distal end.

Suture:

Standard, monofilament nylon suture is used as an aid for retrieval. A loop of suture is trapped by the membrane heat-bond and acts to lead the membrane into the sheath during retrieval. Alternatively, the suture may be replaced by any suitable retrieval aid such as an extension of the membrane itself.

Torquer:

The torquer is used to stabilize the device during packaging, and also as an accessory to help grip and manipulate the shaft during use. It is a standard product used to grip guide-wires up to 0.038" in diameter and employs a simple rotating clamp to lock onto the shaft. The function is similar to a pin-vise.

Loading Tool:

The loading tool is a blunt-tipped, 6F introducer sheath that allows for the device to be flushed and back-loaded. It consists of a silicone hemostasis valve connected to a flush port (with stopcock) and length of Pebax tubing. The device is initially collapsed into the loading tool to evacuate all air and provide a means of passing the hemostasis valve at the proximal end of the sheath.

The present invention comprises a deflector umbrella. In use, the device is placed into the aortic arch by the Seldinger or other technique, through the right arm using either a brachial or radial artery approach. It is advanced to the ostium of the brachiocephalic artery where it is deployed in the aortic arch. The device is then pulled back into position to cover the ostia of both the brachiocephalic and left common carotid arteries. A slow flush of contrast confirms the seal over these two head vessels. The device can remain in place throughout the emboli causing index procedure and then is removed. Alternatively, the device may be emplaced using an aortic puncture, direct surgical placement, or similar route.

The device is retrieved into the sheath by simply pulling back on the shaft relative to the sheath. The central struts fold together in the first action, then a second fold occurs as the sheath forces the petal tips to be closed together. Once the device is fully captured inside of the sheath, the user continues to withdraw it through the hemostasis valve at the proximal end. Variations on the procedure could be employed to minimize intimal damage and/or potential for release of emboli during retrieval. One such procedural variation would be for the user to advance the device and sheath tip into the aorta near the lesser curve of the arch, then re-sheath the device in that location.

A radiopaque marker may be provided on the shaft itself to allow visualization of when the device is fully deployed from the delivery catheter.

The deflector "Embrella" of the present invention is positioned prior to any manipulation of the heart or aortic arch. It is simple to place and carries only the minimal risk of catheterizing the aorta through the arm. The device is opened in the aortic arch and positioned to cover the ostia of both the brachiocephalic and left common carotid arteries. This position prevents emboli from entering the cerebral circulation through either the right or left carotid arteries with one simple device. Any emboli from the cardiac or aortic procedure are deflected downstream. The device, due to its low profile in the aortic lumen, allows passage of catheters, sheaths, or wires used in the index procedure. After the procedure is complete, the device is preferably retracted into the sheath while in the aorta, covering the device prior to withdrawal. Should any clot or debris be attached to the outer side of the device, it will be captured in the closed device and withdrawn.

Deployment:

The device may be deployed through an artery of the arm, or through the femoral artery. The preferred method would be through the right arm, if possible, as this would allow the device to be pulled back against the aortic wall to place it (FIG. 1).

When deployed through the femoral artery (FIG. 2), the opening of the umbrella would be different and the umbrella would be pushed against the aortic wall over the brachiocephalic and left common carotid openings rather than being pulled back. A wire would be cannulated into the brachiocephalic artery in this case to ensure correct positioning of the device. The device would be modified to allow this method of delivery and positioning. In this embodiment, the knob would be on the outside of the umbrella and the handle would be a firm catheter to allow pushing. In this case, retrieval of the device would involve inversion and closing of the "umbrella" by drawstring or another method.

Arm Insertion of the Device:

Referring now to FIG. 1, the deflector is delivered via percutaneous insertion into the right brachial or radial artery and is guided into the aortic arch. There it is deployed and then pulled back into position to cover the ostia of the innominate and left common carotid arteries. The device deflects emboli during aortic and cardiac procedures, allowing the flow of blood through into the cerebral circulation (carotid arteries) but not permitting the passage of emboli greater than 100 microns.

Femoral Artery Insertion of the Device.

Figure 2:
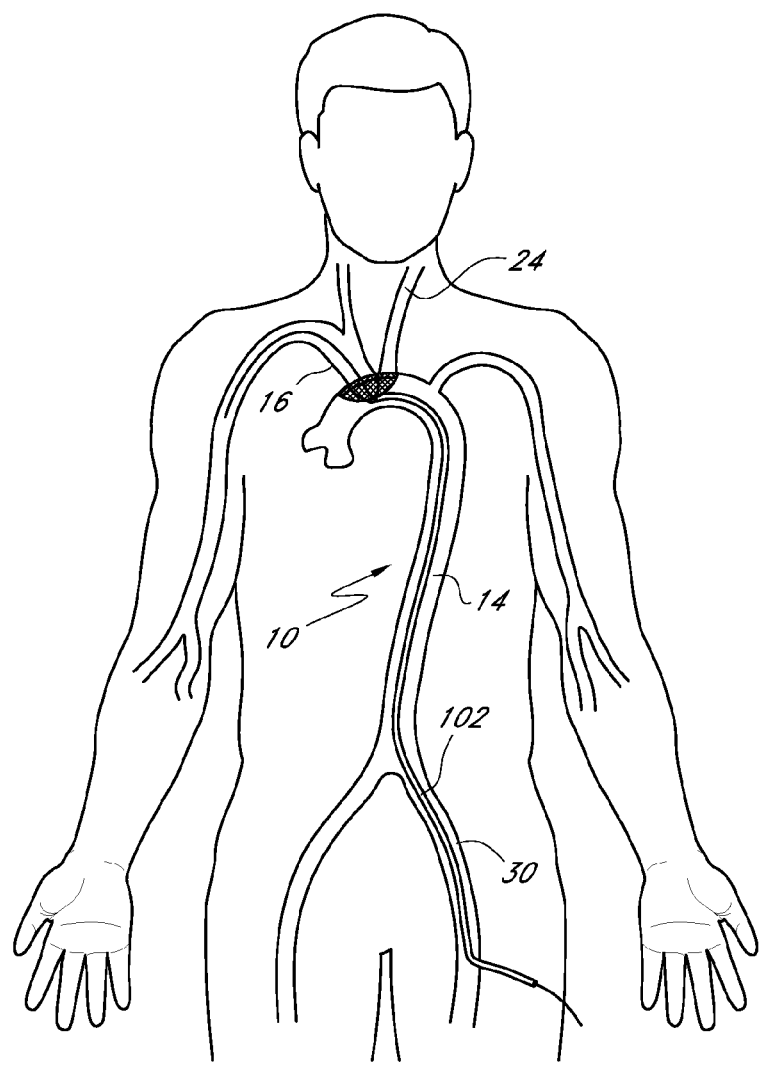
FIG. 2 depicts femoral artery insertion of the deflector of the present invention.

Referring now to FIG. 2, the deflector 100 is delivered via percutaneous insertion into the femoral artery 30 and is guided into the aortic arch 12. After catheterization of the innominate artery 16, the device 100 is passed over the wire and brought into position covering the ostia of the innominate 16 and left common carotid 24 arteries.

Figure 3A:
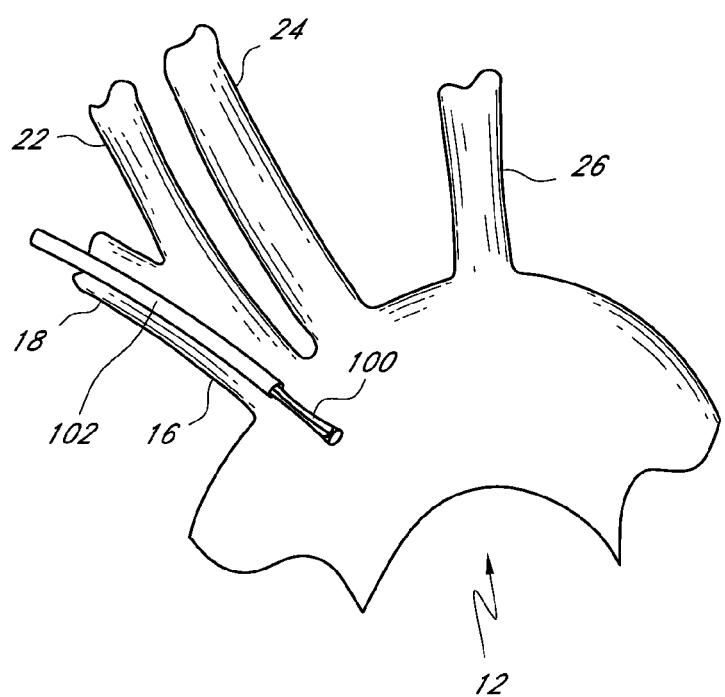
FIGS. 3A-E depict the preferred method of deployment of the deflector of the present invention through the patient's right arm, thus allowing the deflector to be pulled back against the aortic wall to place it.
Figure 3B:
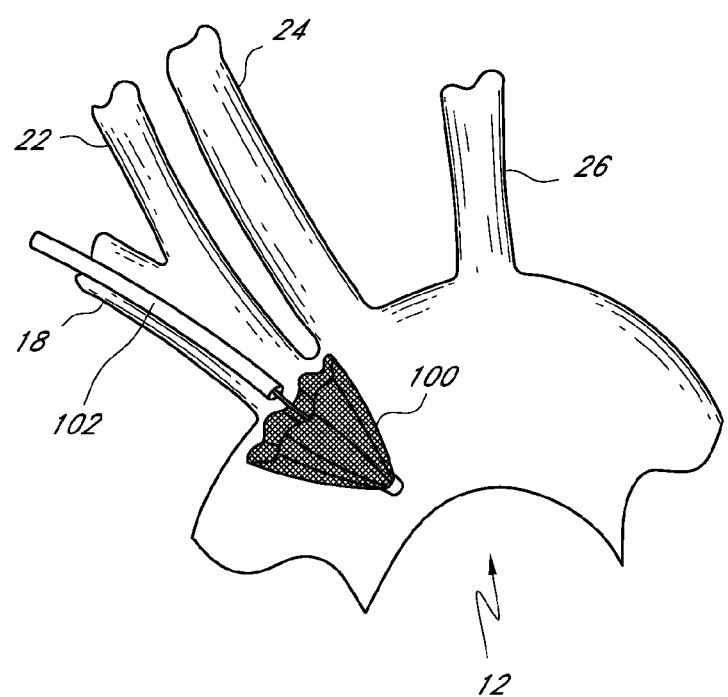
Figure 3C:
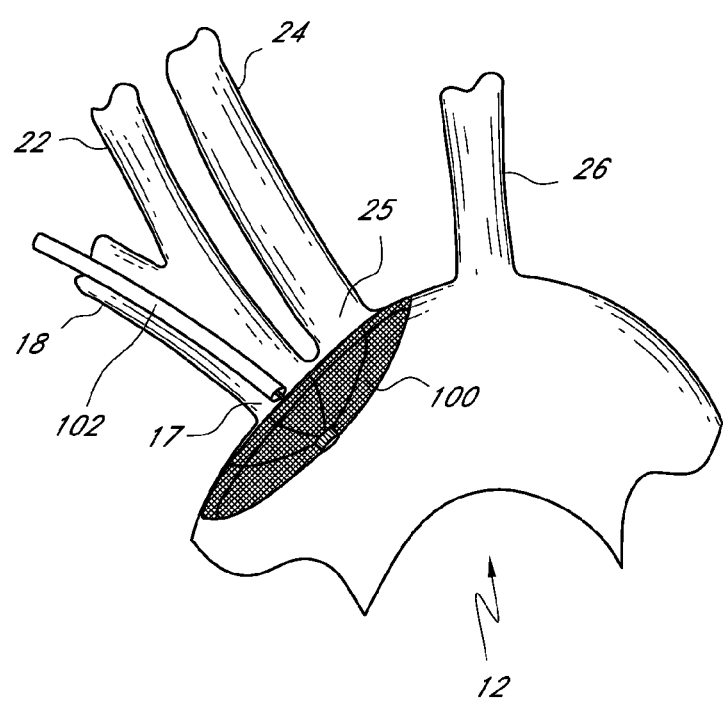
Figure 3D:
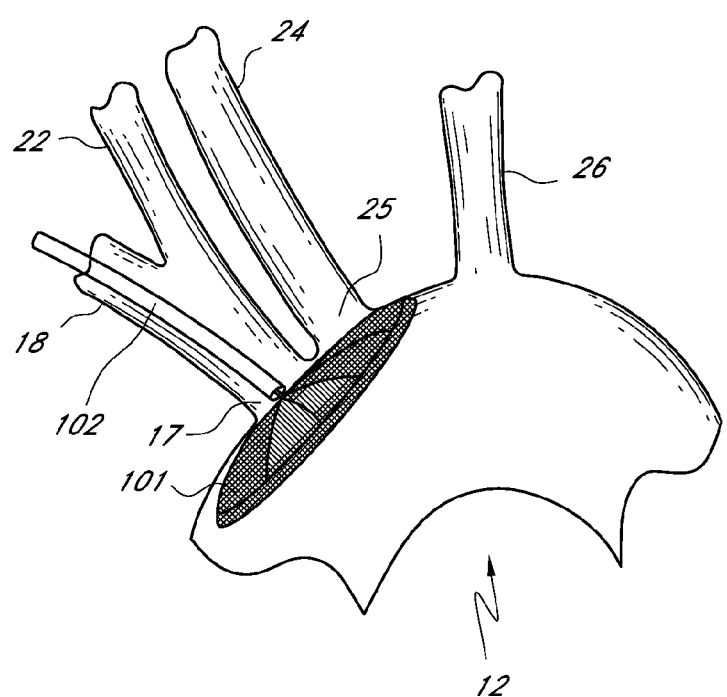
Figure 3E:
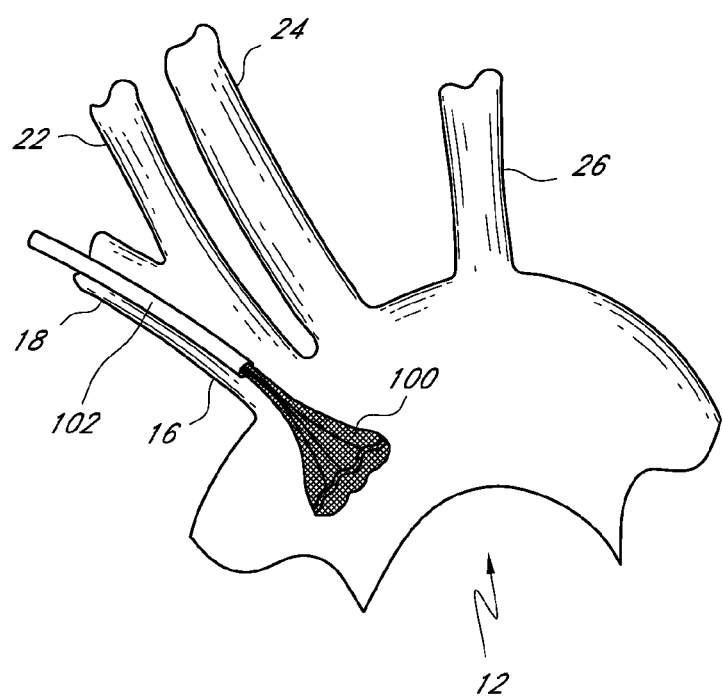

Deployment of the Device Via Arm Approach:

Referring now to FIGS. 3A-E, percutaneous access to the circulation via the right arm is performed and a wire guided into the aortic arch 12 after exiting the innominate artery 16. The device 100 is placed over the wire and guided into the aortic arch 12. The covering outer sheath 102 which encapsulates the device 100 is retracted (FIG. 3A), exposing the device 100 to the aortic bloodstream. The device 100 is then opened in the aortic arch 12 (FIG. 3B). The device 100 is pulled back into position, covering the ostia of the innominate 16 and left common carotid 24 artery. The device 100 allows the passage of blood through to the carotid arteries 22, 24, but deflects debris generated by aortic or cardiac surgery away from these arteries. At the completion of the debris producing concomitant procedure, the device 100 is closed by inverting the covering cap 101 (FIG. 3D). The device 100 is then withdrawn into a covering sheath 102 (FIG. 3E) to completely encapsulate it prior to removal from the arm access artery. Any trapped debris is enfolded within the closed cap 101, safely and securely within the covering sheath 102.

Deployment of the Device Via Femoral Approach.

Figure 4A:
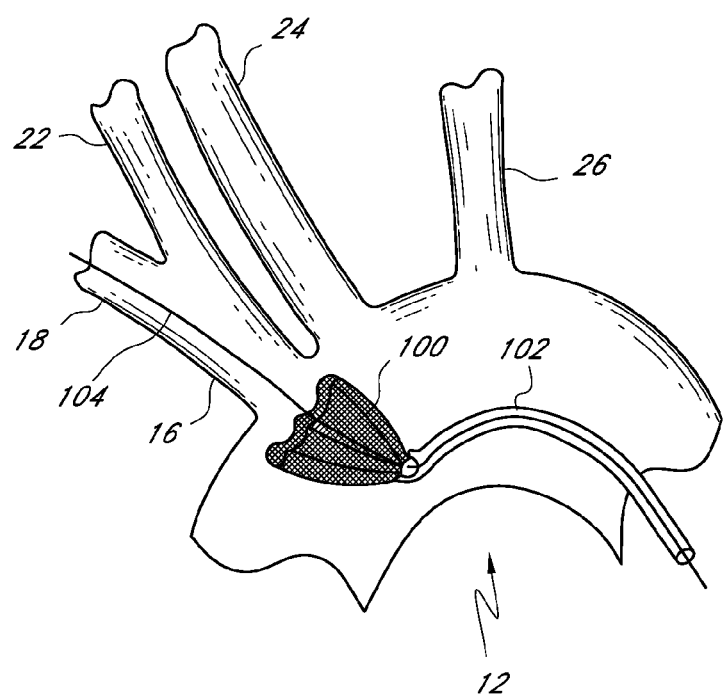
FIGS. 4A-F depict an alternative method of deployment of the deflector of the present invention through the femoral artery wherein the deflector is pushed against the aortic wall over the brachiocephalic and left common carotid openings.
Figure 4B:
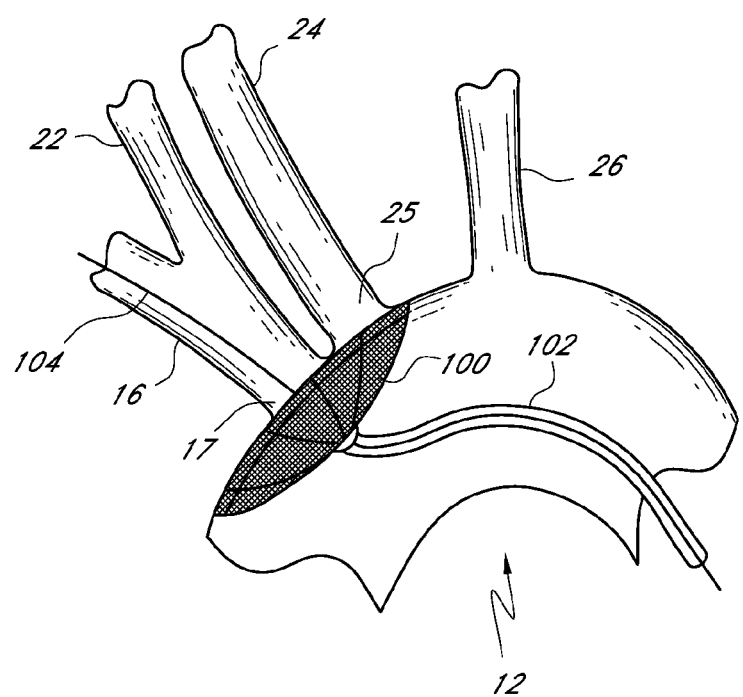
Figure 4C:
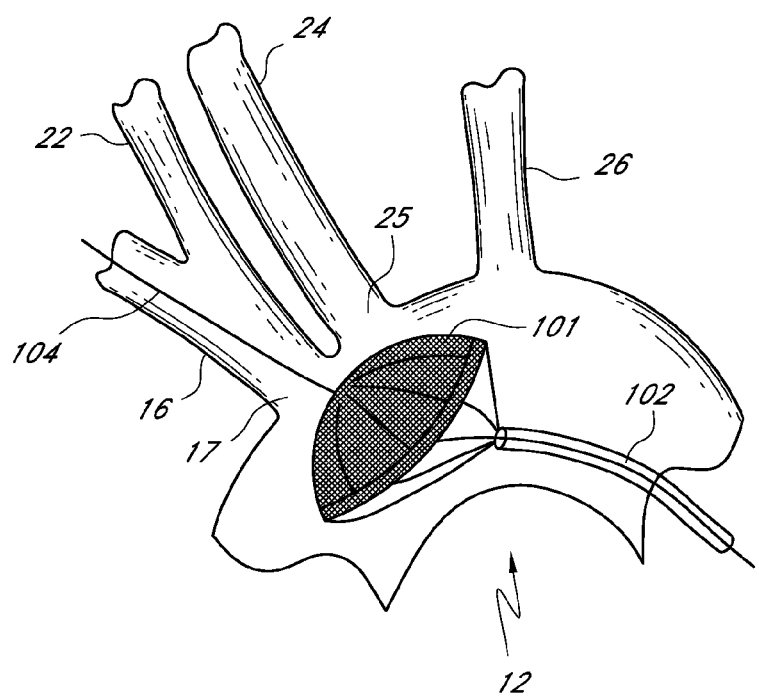
Figure 4D:
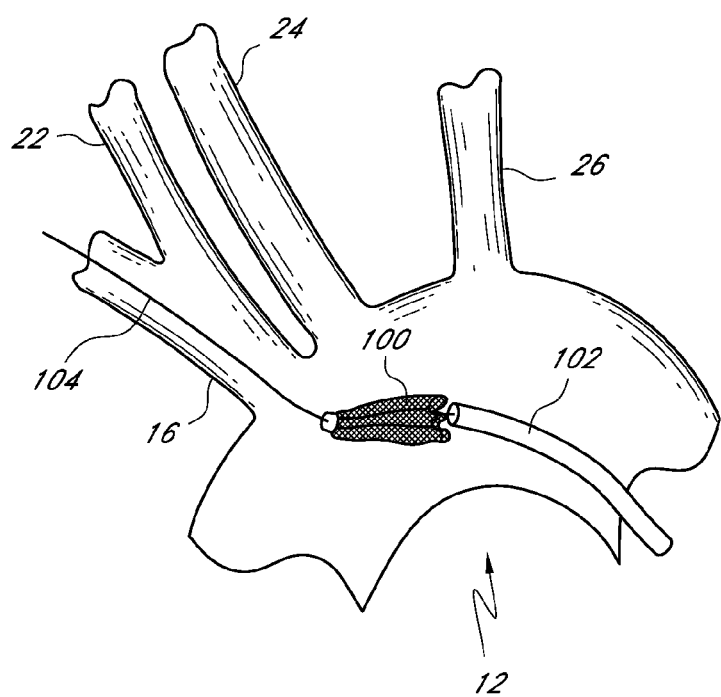
Figure 4E:
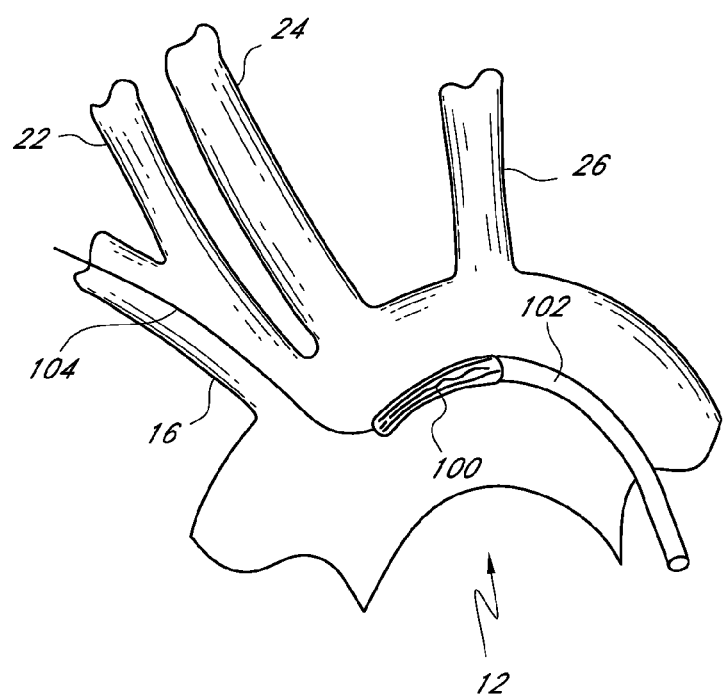
Figure 4F:
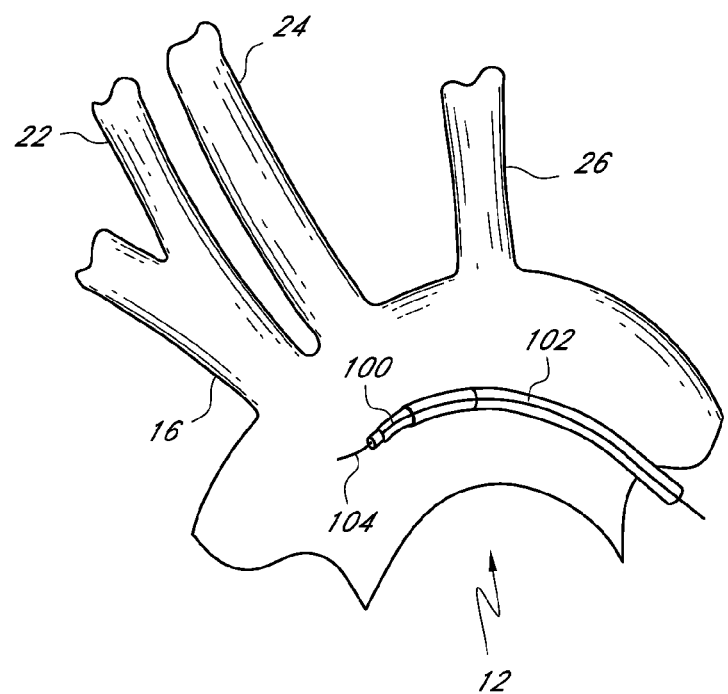

Referring now to FIGS. 4A-F, the innominate artery 16 is catheterized with a wire 104 placed via femoral access. Over the wire 104, the device 100 is guided into position in the aortic arch 12, where it is deployed by unsheathing (FIG. 4A). The device 100 is then pushed over the wire 104 into position securely covering the ostia of the innominate 16 and left common carotid 24 arteries (FIG. 4B). The device 100 allows the passage of blood through to the carotid arteries 22, 24, but deflects debris generated by aortic or cardiac surgery away from these arteries 22, 24. At the completion of the debris producing concomitant procedure, the device 100 is closed by inverting the covering cap 101 (FIG. 4C), shown here by means of drawstrings. The device 100 is then collapsed (FIG. 4D) and withdrawn into a covering sheath 102 (FIG. 4E) to completely encapsulate it prior to removal from the femoral artery 30. Any trapped debris is enfolded within the closed cap 101, safely and securely within the covering sheath 102. The wire 104 and device 100 are then withdrawn from the femoral access.

Direct Insertion of the Device:

The device could also be used with open cardiac or aortic procedures. In these cases, the device could be placed as above or directly into the aorta if the arch were exposed. If it were placed directly, it would be pushed into place as with the femoral approach. Alternatively, any appropriate surgical, percutaneous, or endoscopic procedure may be employed to place the device.

Figure 5A:
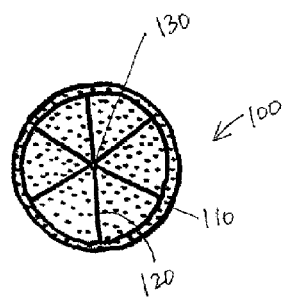
FIGS. 5A-L and 5AA-KK depict various conformations of the deflector of the present invention in plan view (5A-H), phantom plan view (5I-L) and side view (5AA-KK).
Figure 5B:
Figure 5C:
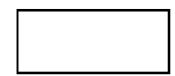
Figure 5D:
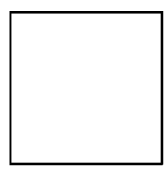
Figure 5E:
Figure 5F:
Figure 5G:
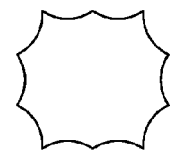
Figure 5H:
Figure 5I:
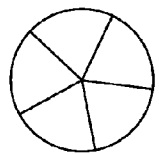
Figure 5J:
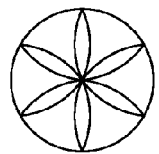
Figure 5K:
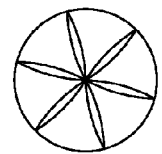
Figure 5L:
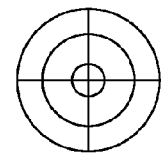
Figure 6A:
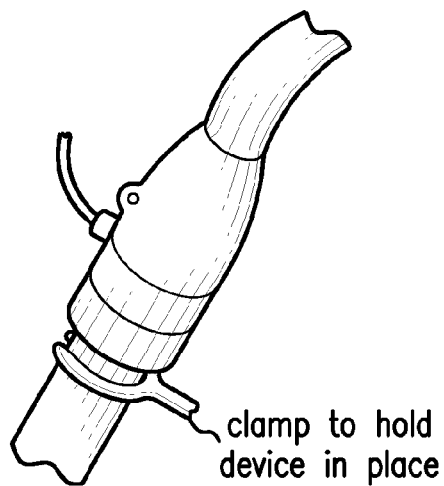
FIGS. 6A-D depict various conformations of the locking mechanism of the present invention.
Figure 6B:
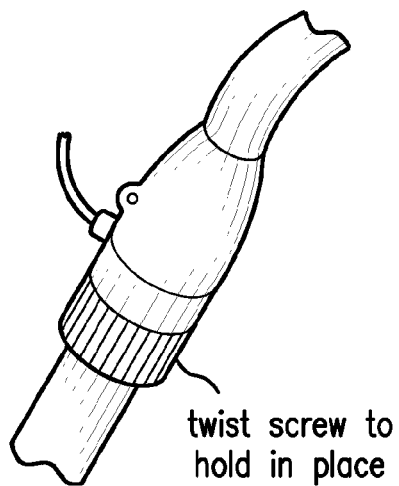
Figure 6C:
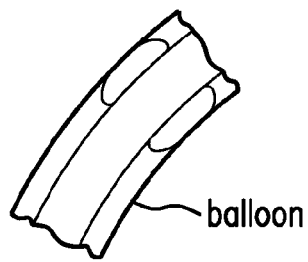
Figure 6D:
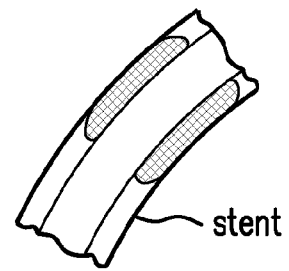
Figure 7A:
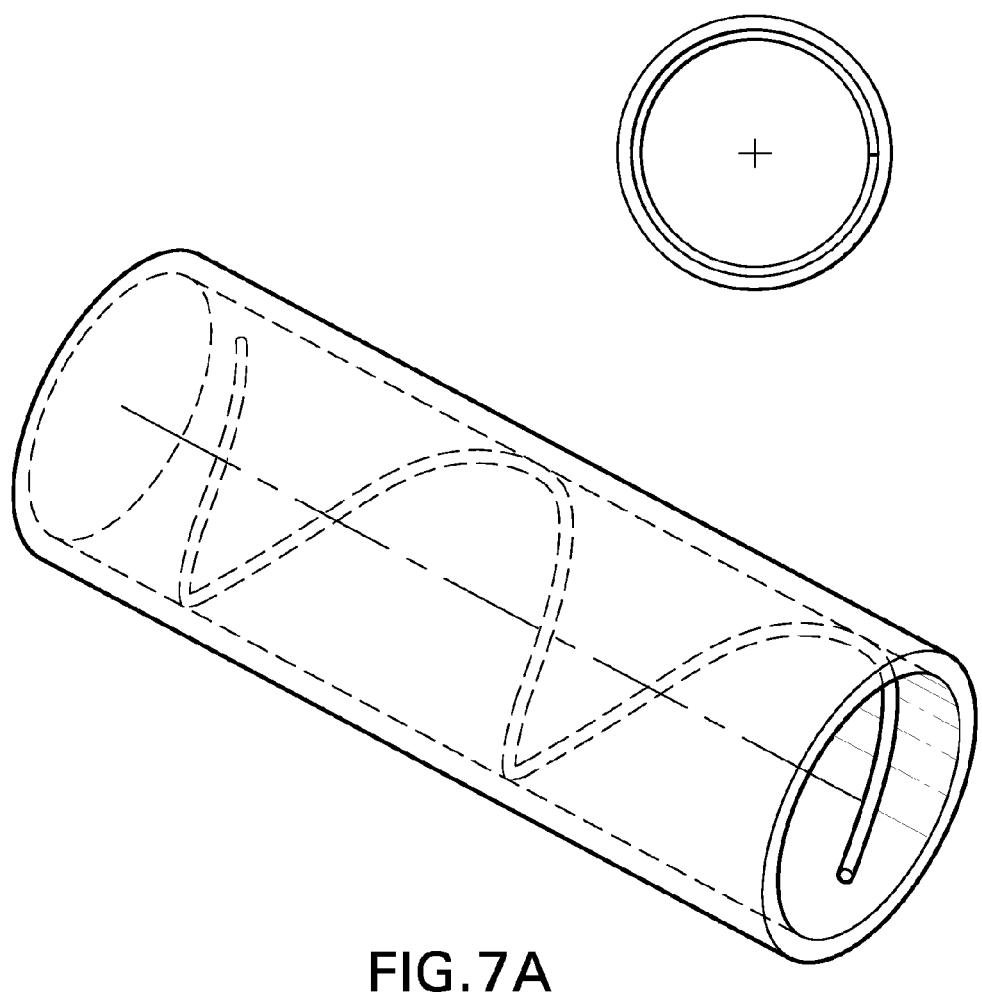
FIGS. 7A-C depict another embodiment of the deflector of the present invention comprising a coil support which expands and flattens upon emergence from the lumen of a tubular containing structure.
Figure 7B:
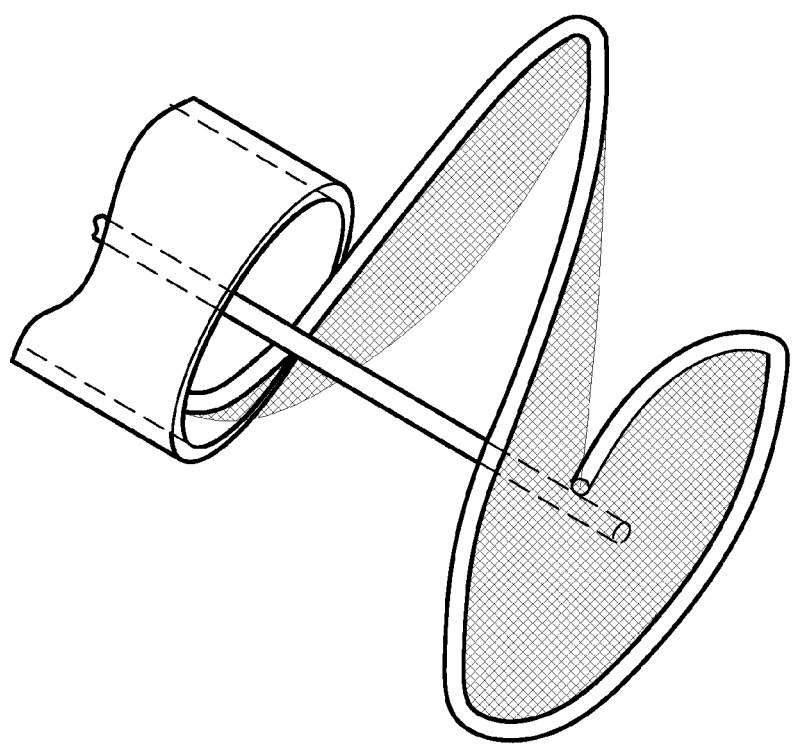
Figure 7C:
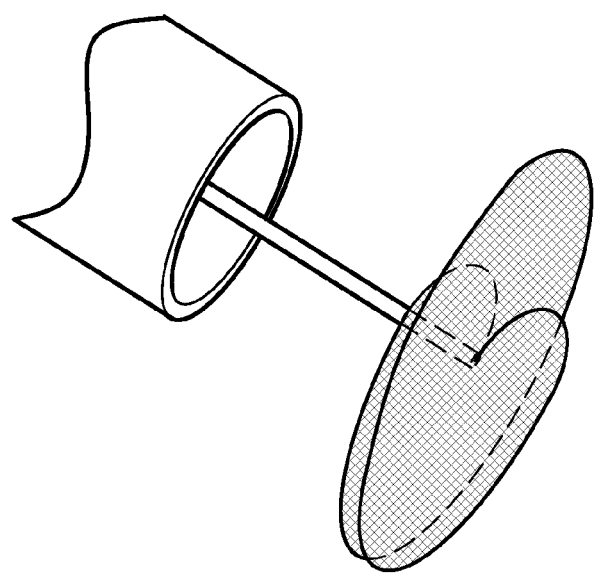
Figure 8C:
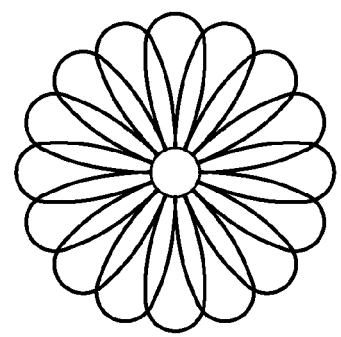
FIGS. 8A-C depict yet another embodiment of the deflector of the present invention comprising a helical, spherical, or onion-shaped mesh that flattens into a disc shape upon emergence from the lumen of a tubular containing structure.
Figure 8B:
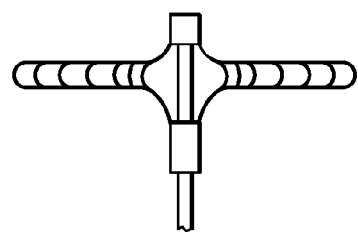
Figure 8A:

Embolic Deflecting Devices:

Referring now to FIG. 5A, one deflector 100 of the present invention, viewed from above, is dome-shaped with an adequate diameter to cover the ostia of both the brachiocephalic 16 and left common carotid 24 arteries, made of a material with pores to allow the flow of blood, but deflect or trap particles of a size which could cause a stroke. The edge 110 of the umbrella 100 is a flexible, porous donut, similar to the edge of a diaphragm, allowing a good seal with the curved aortic wall. The edge 110 will preferably contain a nitinol wire ring. The dome part of the umbrella 100 has struts 120 to assist in the opening and closing of the umbrella 100 and to help maintain its position.

The center of the umbrella has a knob 130 on the inside surface to which the struts 120 are attached. The device 100 is pushed out of the delivery catheter with a tube which engages this knob 130. This knob 130 helps with the opening of the umbrella. The knob 130 remains attached to the umbrella "handle", the guide wire used to pull the umbrella into position. The device 100 may also open as a result of the material it is made of, nitinol or polymer, resuming its shape after being released from its sheath.

The device may also consist of wires which assume their curved dome shape as they are released from the catheter. The porous fabric between the wires is attached at the highest point of the profile to assist with an umbrella-like deflection of clot or debris. The catheter itself may divide at its distal end to comprise the struts of the umbrella deflector. A single wire may be shaped into petal-like struts for the deflector which assume their umbrella shape upon exit from the delivery catheter. The device is constructed of polymer, fabric, metal, or a combination of these materials. The device may be provided with radiopaque markers or metal parts which are radiopaque.

The edge of the umbrella is preferably a flexible, porous donut shape, similar to the edge of a vaginal diaphragm, allowing a good seal with the curved aortic wall. The edge will preferably contain a nitinol wire ring. The dome part of the umbrella preferably has struts or ribs to assist in the opening and closing of the umbrella and to help maintain its position. The center of the umbrella preferably has a knob or similar projection on the inside surface to which the struts are attached. The deflector is pushed out of the delivery catheter with a tube which engages this knob. This knob helps with the opening of the umbrella. The knob remains attached to the umbrella "handle," and the guide wire used to pull the umbrella into position. The device may also be made to open as a result of its construction material, for example, nitinol or polymer, elastically resuming its shape after being released from its sheath.

When the umbrella is to be closed, a tube or sheath of larger diameter than the knob is extended over the guide wire until it engages the knob. The umbrella is pulled back so that it inverts and is enclosed in the tube for removal. Inverting the device assures that no trapped particles escape into the bloodstream.

The device is preferably constructed of polymer, fabric, metal, or a combination of these materials. The device may also optionally be equipped with radio-opaque markers or other structural parts which are radio-opaque for aid in placement guidance.

Another embodiment of the device has a rolled edge. The device may also have a flat porous edge. Another embodiment of the device has no struts, but instead has a nitinol skeleton. Another embodiment has multiple wires to position and anchor the device. Another embodiment of the device has anchors at the edges which help to maintain its position during the procedure.

Another embodiment of the device is parachute-like, with a ring gasket at its edge. The gasket would be held firmly in position over the ostia of the brachiocephalic and left common carotid arteries. The billowy porous middle section would deflect or trap clot and debris on its exterior surface while causing minimal resistance in the aorta. The middle portion would be inverted as it is removed by pulling on wires attached to its center, capturing any clot stuck to it. Alternatively, the center of the device may comprise a screen, which fits more snugly against the aortic wall, with a very small profile, further preventing resistance to downstream aortic blood flow. Again the device would be removed by inversion, capturing any debris stuck to it prior to removal.

Another embodiment of the device comprises a rib-supported or self-supporting spherical shape covered by porous material, which may be distorted into a flat or semi-flat shape for covering the arterial ostia by withdrawing a wire attached to one side of the sphere. The device may be oval or rectangular or of another shape to assist in sealing of the edge against the wall of the aorta, covering the ostia of both the brachiocephalic and left common carotid arteries and maintaining a low profile within the lumen of the aorta. This device could be modified in size in another embodiment in order to be used to cover the ostia of different vessels. The device may be coated with something which prevents clots (e.g. heparin).

The device may be round, oval or rectangular or of another shape to assist in sealing of the edge against the wall of the aorta, covering the ostia of both the brachiocephalic and left common carotid arteries and maintaining a low profile within the lumen of the aorta. This device could be modified in size in another embodiment in order to be used to cover the ostia of different vessels. The device may be coated with something which prevents clots (e.g., heparin).

Another embodiment of the device is barbell shaped, with either a porous balloon or porous filter on opposite ends, or a porous sausage shape that inflates along its long axis. Debris is thus deflected downstream in the blood flow by the mid-section of the device which protrudes into the aortic lumen when the device is properly placed. The porous balloon of the distal end may also be substituted with another shape such as a disc or dome such that the balloon protects the brachiocephalic artery, and the distal portion protects the ostium of the left common carotid artery.

As depicted in FIGS. 5A-5KK, and 7A-C, 8A-C the shape of the device may be oval or rectangular or of another shape to assist in sealing of the edge against the wall of the aorta, covering the ostia of both the brachiocephalic and left common carotid arteries and maintaining a low profile within the lumen of the aorta. The device may have petals or other parts which come together to make the deflector shape.

Materials from which the device of the present invention may be constructed include: metals such as nitinol, Elgiloy, stainless steel, and titanium, and bio-compatible plastics, such as PTFE, ePTFE, polyester, silicone, and nylon.

The deflector of the present invention may take alternative shapes such as: round, oval, square, rectangular, elliptical, and edge-scalloped or irregular.

The depth profiles useful in the present invention are: flat, rounded, peaked, onion shaped, tent shaped, parachute shaped, conic, cylindrical, plateau, disc shaped (flat, concave, convex, or concave-convex, spherical or any shape with a supporting protrusion that may extend to the opposite wall of the aortic lumen.) The device may be single layer, bi-layer, or multi-layer and may be comprised of overlapping or connecting components.

During deployment, the device may be locked in position using a locking mechanism such as is depicted in FIGS. 6A-D comprising: a clamp (6A); a twist screw with our without a ratchet (6B); a balloon (6C); or a stent-like sleeve (6D).

Possible methods of deployment of the device include opening an umbrella (with or without struts), overlapping of opening petals (blooming), opening of overlapping elements as in an iris, memory-restoration of a preformed shape, mushrooming, expansion of pores or cells, and release of supporting elements that form the peripheral shape with porous material stretched between.

Figure 9:
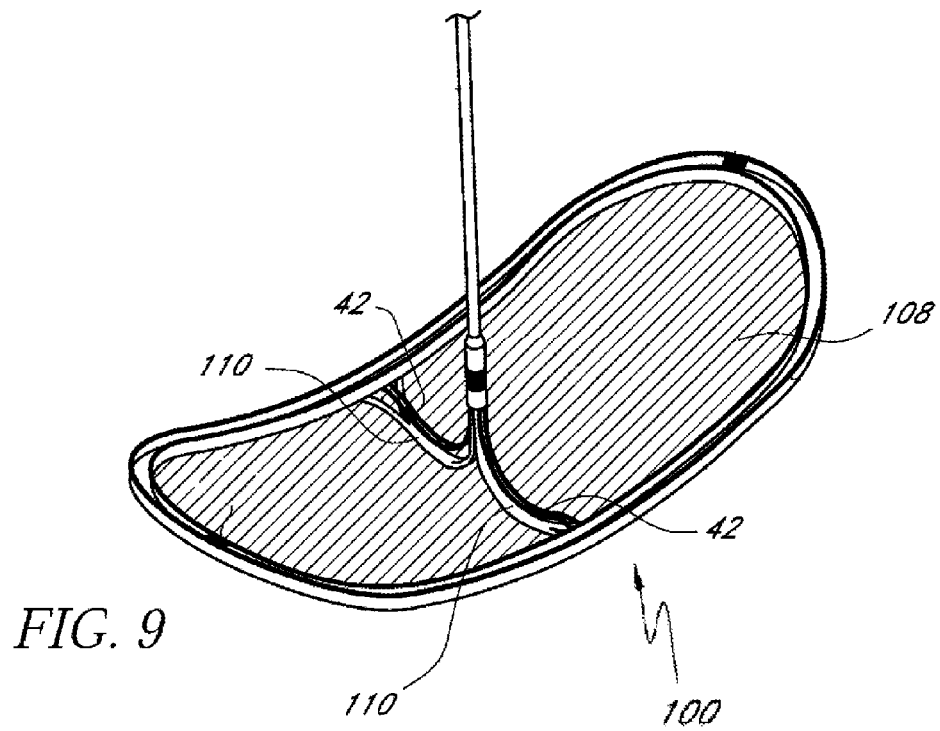
FIG. 9 is a perspective view of a preferred embolic deflecting device.

Preferred Embolic Deflecting Device:

FIG. 9 shows a preferred embodiment of the device 100 is composed an oval nitinol frame 110 with an adequate diameter of about 60 mm to cover the ostia of both the brachiocephalic and left common carotid arteries. This device could be modified in size in another embodiment in order to be used to cover the ostia of different vessels, including all three head vessels including the left subclavian artery 26. Such a device may be asymmetric in the major dimension. Alternatively, a smaller device may be deployed to cover the ostium of only one vessel.

The porous membrane 108 attached to the center of the frame is made of a polyurethane with about 100 micron or smaller pores to allow the flow of blood into the cerebral circulation, but able to deflect and/or trap emboli of a size which could cause a stroke. The frame 110 of the device is preferably a nitinol wire, allowing a good seal with the curved aortic wall. The center of the device may comprise a porous membrane or screen 108, which fits more snugly against the aortic wall, with a very small profile, further preventing resistance to downstream aortic blood flow. In profile, the device may be flat, concave, or convex. The device opens as a result of its construction material, nitinol, elastically resuming its shape after being released from its sheath. Retrieval involves simply retracting the device back into the sheath by pulling on it, or by first advancing it slightly to separate the edges from the vessel wall before pulling back.

Figure 18:
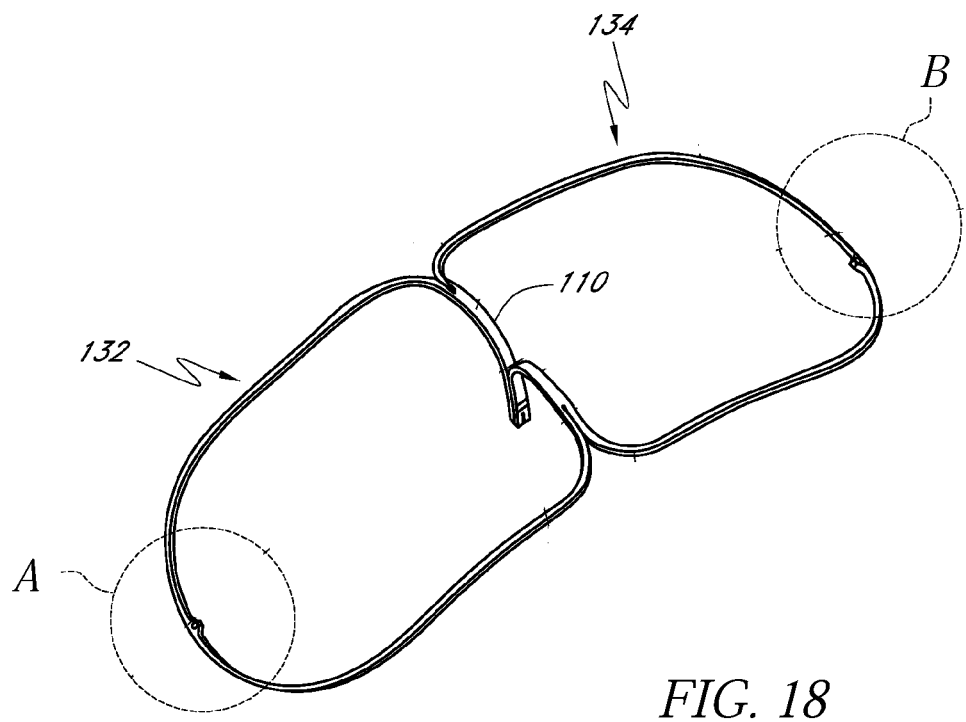
FIG. 18 shows the a perspective view of a collapsible frame of the preferred embolic deflecting device.
Figure 19:
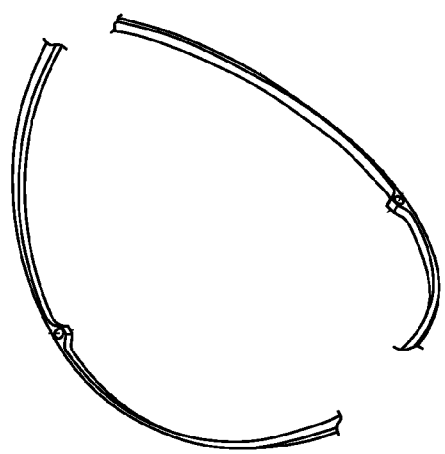
FIG. 19 are enlarged views of details A and B from FIG. 18.

The frame 110 may be formed in a single piece which is cut and formed from sheet stock. The porous membrane is wrapped around the frame and heat-sealed to itself. A suture loop 42 trapped under the porous membrane which is sealed to the frame aids in retrieval. FIG. 18 shows a perspective view of a collapsible frame 110 of the preferred embolic deflecting device, while FIG. 19 are enlarged views of details A and B from FIG. 18. Radiopaque markers are provided at points A and B on the frame.

Figure 10:
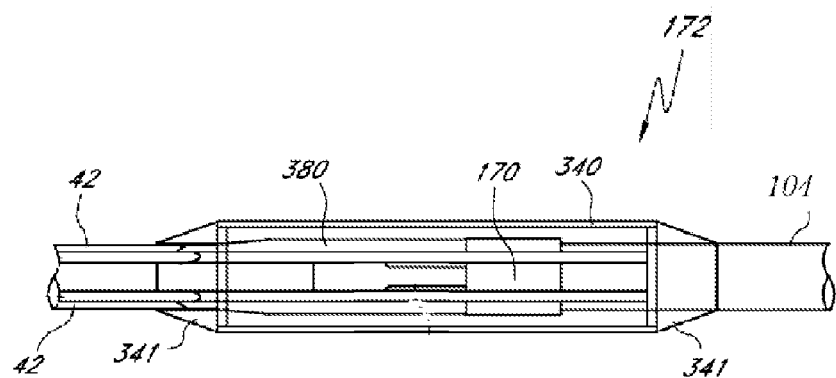
FIG. 10 shows a shaft connection leading to the embolic deflecting device of FIG. 9.
Figure 11:
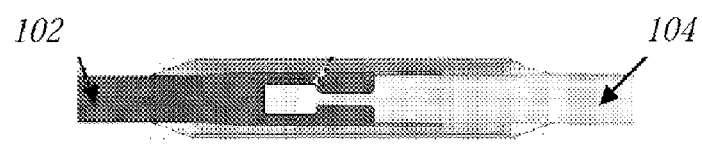
FIG. 11 is a sectional view of the shaft connection of FIG. 10.

FIG. 10 shows a shaft connection 172 leading to the embolic deflecting device 100 of FIG. 9, and FIG. 11 is a sectional view of the shaft connection. The shaft 104 includes a Nitnol wire shaft of 0.035" diameter and couples to a proximal strut 380 of the formed frame 110. A hypotube 340 houses a frame-shaft joint, the hypotube being show transparent. A proximal end of the hypotube is crimped around the connection to lock the assembly together including a radiopaque marker 170 provided for positioning at the sheath tip. Fillets of UV adhesive 341 seal the shaft connection and make for sooth transitions at each end thereof. The retrieval sutures 42 extend back from the frame and are anchored at the shaft connection.

Figure 12:
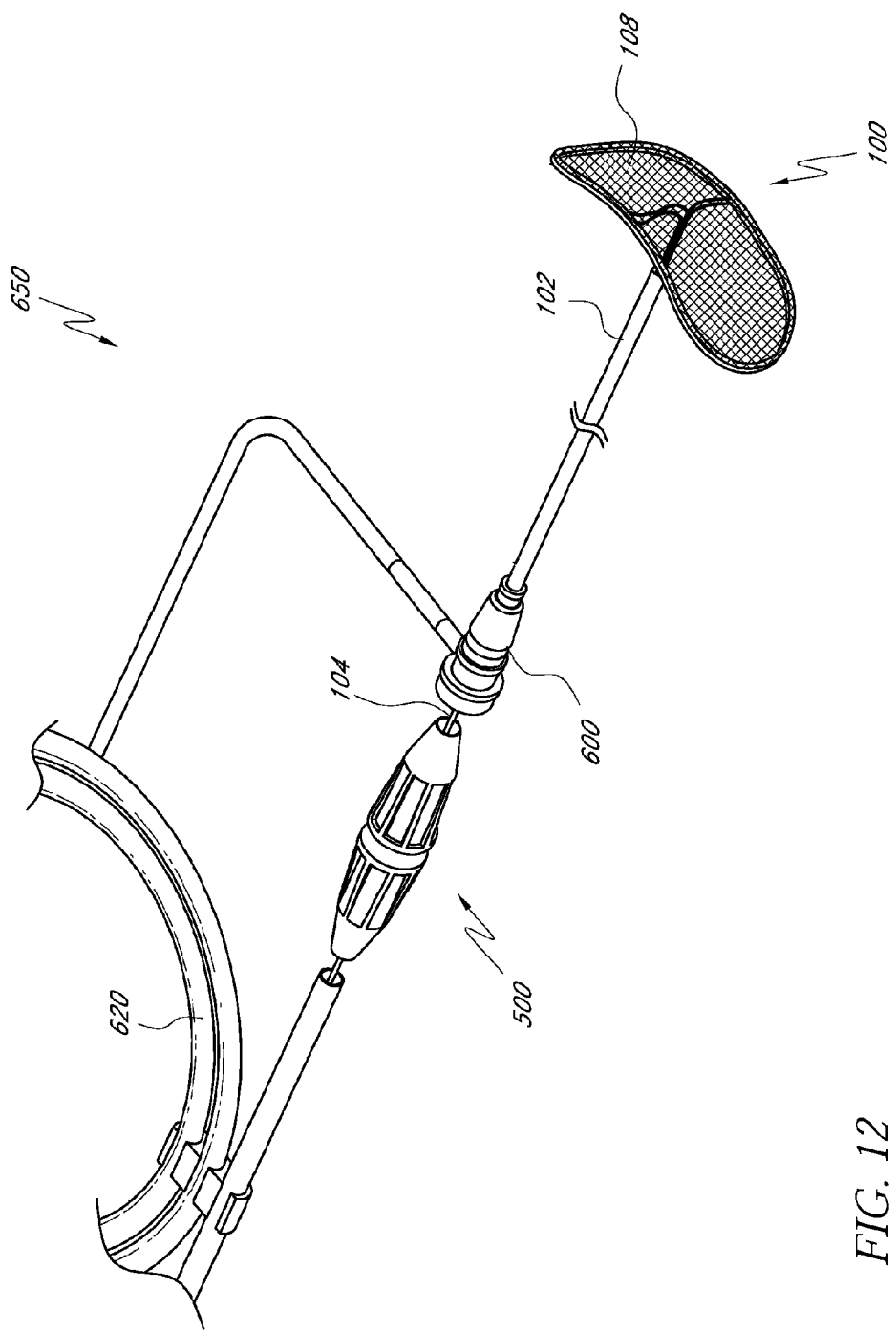
FIG. 12 is a perspective view of an assembly of parts used with the embolic deflecting device of FIG. 9.

FIG. 12 is a perspective view of an assembly of parts 650 used with the embolic deflecting device 100 of FIG. 9. The Nitinol shaft is coiled into a hoop 620 and passes through a guidewire torquer 500 just before a loading tool 600. The guidewire torquer 500 helps stabilize the assembly in packaging and is used to manipulate the device 100 during the procedure. The embolic deflecting device 100 is packaged with the loading tool 600 on the shaft 102 ready to be loaded. The loading tool has a side port and hemostasis valve that allows for flushing and aspiration.

Figure 13:
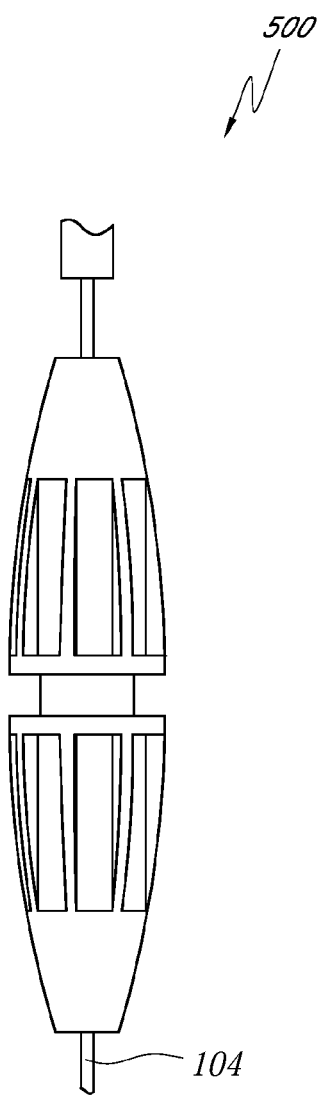
FIG. 13 is an enlarged view of a guidewire torquer shown in FIG. 12 used to manipulate the embolic deflecting device of FIG. 9.

The guidewire torquer 500 shown enlarged in FIG. 13 can be used because of the 0.035" wire diameter 104. The torquer manipulates the device and provides an option to use a cross-cut valve instead of a Touhy-Borst adapter for locking the device in place.

Figure 14:
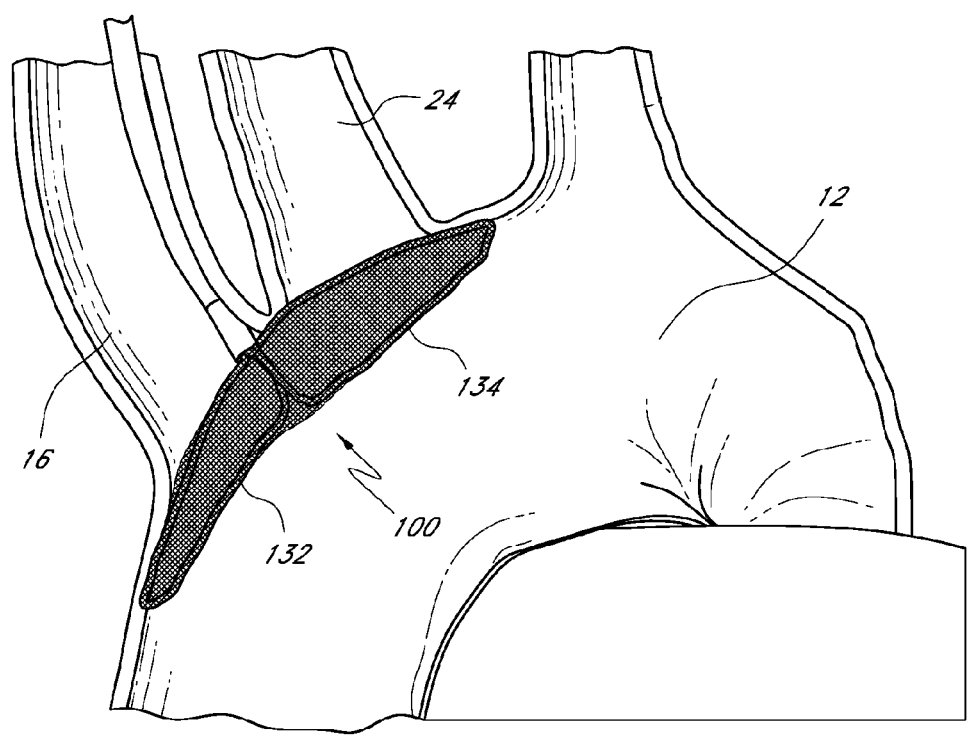
FIG. 14 shows the embolic deflecting device of FIG. 9 in place in the aorta.
Figure 15:
FIG. 15 shows the embolic deflecting device in place in the aorta with a separate catheter passing over the aortic arch, and also showing emboli in the aorta.
Figure 16:
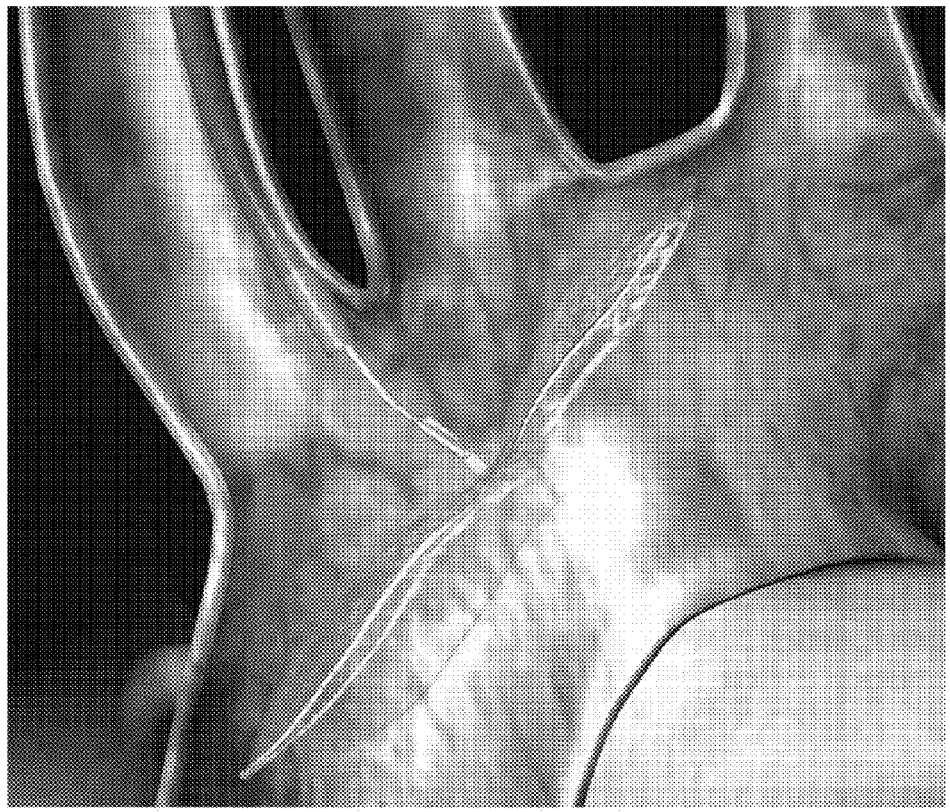
FIG. 16 shows the embolic deflecting device being readied for recovery by advancing a proximal shaft into the aortic lumen.
Figure 17:
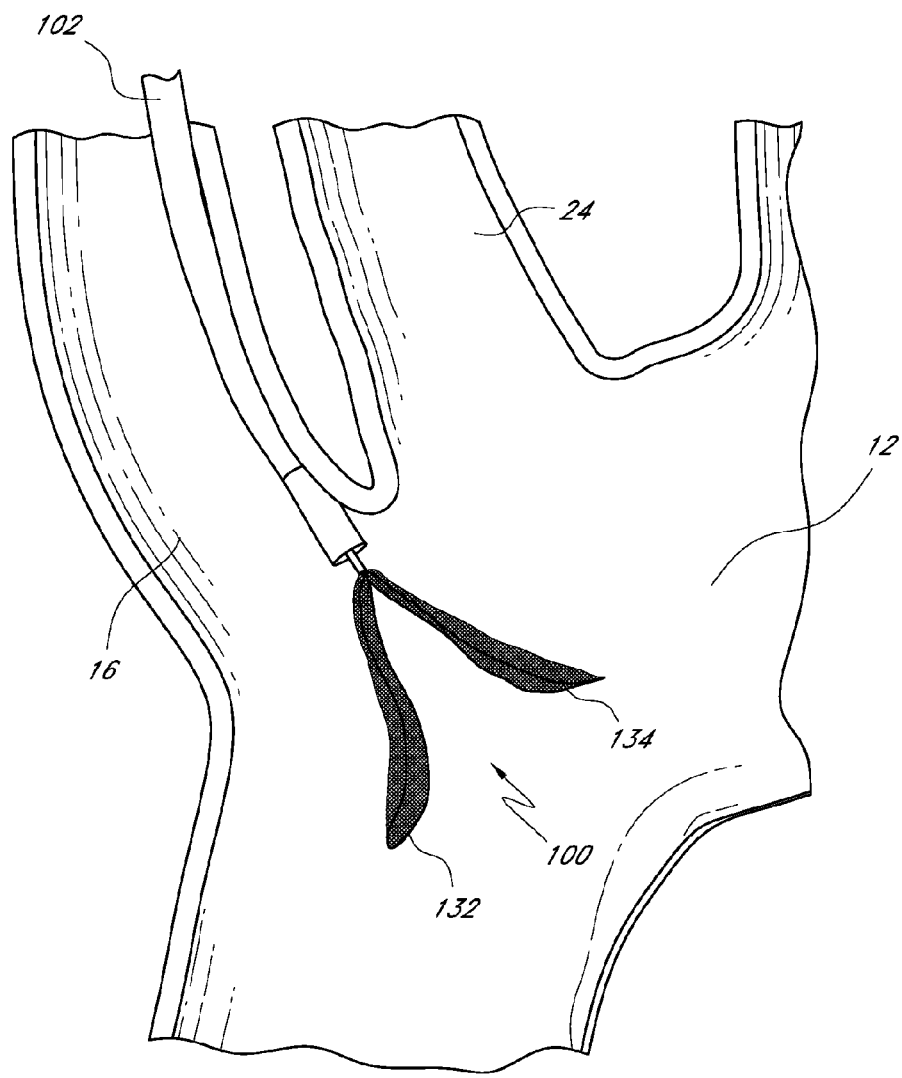
FIG. 17 shows the embolic deflecting device in an intermediate position during either deployment or recapture into the catheter, controlled by shaft advancement or retraction.

FIGS. 14-17 show the embolic deflecting device 100 of FIG. 9 in various placements in the aorta. Specifically, FIG. 14 shows the embolic deflecting device of FIG. 9 in place in the aorta 12, while FIG. 15 shows the same position with a separate catheter passing over the aortic arch, and also showing emboli in the aorta. In FIG. 16 the embolic deflecting device is being readied for recovery by advancing a proximal shaft 102 into the aortic lumen, and FIG. 17 shows the embolic deflecting device in an intermediate position during either deployment or recapture into the catheter, controlled by shaft advancement or retraction.

Percutaneous access to the circulation via the right arm through the radial or brachial artery 16 is performed and a wire guided into the aortic arch after exiting the innominate artery. The device 100 is inserted into a loading tool, then into a 6F sheath, placed over the wire, and guided into the aortic arch. The device is pushed out of the sheath and then opened in the aortic arch (FIG. 16). The device is pulled back into position, covering the ostia of both the innominate and left common carotid arteries 24. The device allows the passage of blood through to the carotid arteries, but deflects emboli generated by aortic or cardiac procedures away from these arteries. At the completion of the debris producing concomitant procedure, the device is closed. Preferably, the device is then withdrawn into a covering sheath (FIG. 17) to encapsulate it prior to removal from the arm access artery. Any trapped debris is enfolded within the closed device, safely and securely within the covering sheath.

Referring now to FIG. 17, the device opens by "blooming" its two lobes or "petals" 132, 134 as the shaft is extended beyond the sheath. In this manner, the device does not contact the aortic wall, and thus, does not contribute to dislodgement of embolic particulate debris during emplacement. The same mechanism is true during retrieval. Referring now to FIG. 18, the deflector of the present invention, viewed from above, is oval shaped with a diameter of 60 mm to cover the ostia of both the brachiocephalic and left common carotid arteries in most patients. It can also be made a different size. It is composed of a nitinol frame supporting a membrane 108 made of a polyurethane laser drilled with 100 micron pores (or another size pores) to allow the flow of blood, but deflect or trap emboli of a size which could cause a stroke. The frame of the device is a flexible nitinol skeleton allowing a good seal with the double curvature of the aortic wall. The device opens as a result of the material from which it is made, nitinol, resuming its shape after being released from its sheath. The device is oval to assist in sealing of the edge against the wall of the aorta, covering the ostia of both the brachiocephalic 16 and left common carotid arteries 24 and maintaining a low profile within the lumen of the aorta. The center of the device is a porous membrane which, like a screen, fits snugly against the aortic wall, with a very small profile, further preventing resistance to flow in the aorta and also allowing passage of index procedure wires, catheters and sheaths. This device could be modified in size or shape in another embodiment in order to be used to cover the ostia of different vessels. The device is coated with heparin to prevent clotting, but may be uncoated or coated with another substance. The device is provided with radioopaque markers shown in FIGS. 18 and 19.

During deployment, the device may be locked in position related to the sheath using a rotating valve or similar mechanism. The sheath is preferably held in position at the skin using Tegaderm. The device remains tethered by the shaft, and tensioned against the vessel wall by application of force external to the patient. The device and/or shaft may be elastic to accommodate movement or shifting during use, so as to maintain protection of the head vessels. The device is preferably tethered to permit repositioning or removal at any time.

While the invention has been described in its preferred embodiment, it is to be understood that the words which have been used are words of description rather than of limitation and that changes may be made within the purview of the appended claims without departing from the true scope and spirit of the invention in its broader aspects. Rather, various modifications may be made in the details within the scope and range of equivalents of the claims and without departing from the spirit of the invention. The inventor further requires that the scope accorded the claims to be filed be in accordance with the broadest possible construction available under the law as it exists on the date of filing thereof and that no narrowing of the scope of the appended claims be allowed due to subsequent changes in the law, as such a narrowing would constitute an ex post facto adjudication, and a taking without due process or just compensation.

I claim:

1. An embolus deflector for protecting against cerebral embolization, the embolus deflector being deployable from a first ostium of the aortic arch selected from the group consisting of an ostium of a right common carotid artery, an ostium of a left common carotid artery, and an ostium of a brachiocephalic artery, the embolus deflector comprising a blood-flow-permeable covering configured to simultaneously extend over the first ostium and a second one of the group of ostiums, wherein the embolus deflector comprises:
 a hollow sheath;
 a generally elongated shaft, the shaft having a distal end and a proximal end and being arranged to pass through and be displaced linearly within the hollow sheath;
 an expandable shield extending from the shaft distal end, the expandable shield having an open configuration and a closed configuration, the expandable shield comprising a first petal and a second petal, the expandable shield comprising:
  a Nitinol expandable support frame extending from the shaft distal end, wherein the support frame comprises a first petal frame and a second petal frame, wherein the first petal frame defines a perimeter of the first petal and is dimensioned, when the expandable shield is in the open configuration, to define a first petal area of sufficient size to extend across and cover the first ostium, and wherein the second petal frame defines a perimeter of the second petal and is dimensioned, when the expandable shield is in the open configuration, to define a second petal area of sufficient size to extend across and cover the second ostium, the first and second petal frames extending in opposite longitudinal directions from laterally outward ends of a pair of proximal struts of the support frame that attach to the shaft distal end, the proximal struts diverging in lateral directions from each other so that the first and second petal frames define an oval periphery of the support frame consisting of just the first and second petals;

porous material extending across the first petal area and across the second petal area, wherein the porous material comprises a membrane having pores with individual diameters of 100 micron or less; and a loop of bio-compatible plastic monofilament suture secured to the expandable support frame, ends of the loop of suture secured to the distal end of the elongated shaft, and the loop of suture operable to collapse the expandable shield for retrieval when the shaft is retracted within the sheath;

wherein the expandable shield in the closed configuration is sized and configured to be advanced through the sheath, and the expandable shield is sized and configured to be converted from the closed configuration to the open configuration within the aortic arch, wherein in the closed configuration the first and second petals are held against each other in general longitudinal alignment with the shaft, and in the open configuration the first and second petals extend substantially radially away from each other and substantially radially away from the distal end of the shaft and define the oval periphery, wherein in the open configuration the expandable shield is sized and configured to be positioned within the aortic arch and against the aortic wall such that the expanded first petal extends over the first ostium while the expanded second petal simultaneously extends over the second ostium, wherein the expandable shield presents a low profile against the aortic wall and within a lumen of the aortic arch to thereby cause minimal resistance to blood flow in the aortic arch by permitting blood to flow through the aortic arch past the expandable shield and also to allow sheaths, catheters, or wires to pass through the aortic arch and past the expandable shield without passing therethrough.

2. The deflector of claim 1 wherein the expandable shield is capable of being inserted and placed through a catheter in an artery of the arm of a patient.

3. The deflector of claim 2 wherein the artery is the brachial artery of a patient, the first ostium is the ostium of the brachiocephalic artery, and the second ostium is the ostium of the left common carotid artery.

4. The deflector of claim 1 wherein the expandable shield is capable of being inserted and placed through a catheter in the femoral artery of a patient.

5. The deflector of claim 1 wherein the expandable shield is capable of being inserted and placed directly into the aorta of a patient during an open surgical procedure.

6. The deflector of claim 1 wherein prior to withdrawal, the expandable shield may be inverted, trapping debris.

7. The deflector of claim 1 wherein prior to withdrawal, the expandable shield may be closed, trapping debris.

8. The deflector of claim 1 further including a radiopaque marker attached to outer ends of each of the first and second petals of the support frame.

9. The deflector of claim 1 wherein the porous material consists of a polyurethane membrane with laser-drilled pores.

10. The device of claim 1, wherein the first and second petals when expanded together form a substantially oval shape with a long dimension of about 60 mm.

11. The device of claim 1, wherein the nitinol support frame comprises different thicknesses along the perimeter of the first petal frame to provide varying stiffness therearound.

12. A method of employing an emboli deflector to cover an ostium of a brachiocephalic artery and an ostium of a left common carotid artery, the method comprising the steps of:

a. Accessing the circulation through percutaneous insertion of a catheter into an artery in an arm of a patient;

b. Advancing a deflection device through the artery into an aortic arch through the ostium of the brachiocephalic (innominate) artery, the deflection device having a hollow sheath within which slides a deflector in a collapsed configuration coupled to a distal end of a shaft, the hollow sheath including a proximal end defining a hemostasis valve through which the shaft passes, the shaft further having a torquer locked thereon that permits gripping and manipulation of the shaft during use;

c. Using the torquer and shaft, advancing the shaft and deflector in its collapsed configuration through the sheath, wherein the deflector comprises a Nitinol expandable support frame with only first and second petals extending in opposite longitudinal directions from laterally outward ends of a pair of proximal struts of the support frame that attach to the shaft distal end, the deflector comprising the collapsed configuration and an expanded configuration, wherein the petals, when expanded, are positioned in adjacent fashion, radially extending from opposite sides of the shaft to form the expanded deflector;

d. Advancing the deflector from within the sheath in the aortic arch so as to permit expansion of the deflector within the aortic arch, wherein expansion of the deflector involves the two petals expanding to radially extend away from each other to form an oval-shaped continuous porous surface that has a longitudinal dimension greater than a lateral dimension;

e. Positioning the deflector by manipulating the petals using the torquer to simultaneously cover the ostium of the brachiocephalic artery and the ostium of the left common carotid artery with the substantially continuous porous surface;

f. Sealing an edge of the deflector to a wall of the aortic arch with the porous surface against the wall of the aortic arch; and g. Retracting the shaft to pull a loop of bio-compatible plastic monofilament suture secured to the shaft and to the deflector to collapse the deflector for retrieval within the sheath.

13. The method of claim 12 further comprising the steps of:

h. Performing a cardiac or vascular interventional medical procedure;

i. Inverting the deflector into a sheath or closing it in a manner to trap any debris or clot remaining on the device surface; and j. Withdrawing the inverted or closed deflector from the patient.

14. The method of claim 12, wherein positioning the deflector to simultaneously cover the ostium of the brachiocephalic artery and the ostium of the left common carotid artery comprises simultaneously leaving the ostium of a left subclavian artery uncovered.

15. The method of claim 12, wherein positioning the deflector comprises retracting the deflector toward the ostium of the brachiocephalic artery.

16. The method of claim 12, wherein the plurality of petals comprises a first petal and a second petal, wherein the first petal is sized and configured to cover the ostium of the brachiocephalic artery, and the second petal is sized and configured to cover the ostium of the left common carotid artery.

* * * * *